United States Patent [19]

Feinbloom et al.

[11] Patent Number: 4,863,468
[45] Date of Patent: Sep. 5, 1989

[54] UNIVERSALLY ADJUSTABLE TELESCOPIC SPECTACLE ASSEMBLY FOR USE WITH IMPLANTED INTRAOCULAR LENSES AND ASSOCIATED METHODS

[75] Inventors: Richard E. Feinbloom, New York, N.Y.; David B. Soll, Rydal, Pa.

[73] Assignee: Designs for Vision, Inc., Ronkonkoma, N.Y.

[21] Appl. No.: 128,921

[22] Filed: Dec. 4, 1987

[51] Int. Cl.⁴ .................................. A61F 2/16
[52] U.S. Cl. ........................................ 623/6; 351/120; 351/158
[58] Field of Search ............... 623/6; 351/204, 120, 351/158

[56] References Cited

U.S. PATENT DOCUMENTS

| | | | |
|---|---|---|---|
| 4,364,645 | 12/1982 | Feinbloom | 351/120 X |
| 4,666,446 | 5/1987 | Koziol et al. | 623/6 |
| 4,710,197 | 12/1987 | Donn et al. | 623/6 |

Primary Examiner—Ronald L. Frinks
Attorney, Agent, or Firm—Arthur L. Plevy

[57] ABSTRACT

A universally adjustable telescopic spectacle assembly for use with an implanted intraocular lens employs an objective lens which has positioned in front of the objective lens a cylindrical lens to provide cylindrical correction to the handicapped user. The telescopic assembly employs universal motion in that the assembly can be moved with respect to a spectacle frame so that one is able to shift the objective lens axis about a central point while further having the capability of moving the objective lens in a spiral motion away from or towards the eye of the user and further having means for providing a pivotal joint mechanism to permit maximum oblique adjustment of the entire telescopic assembly as related to the optical or central axis of the objective lens. In this manner any change in conditions of vision or a misalignment of the intraocular lens as inserted during surgery can be compensated for by the universal adjustable telescopic assembly as disclosed.

20 Claims, 2 Drawing Sheets

ABLE TELESCOPIC
SPECTACLE ASSEMBLY FOR USE WITH
IMPLANTED INTRAOCULAR LENSES AND
ASSOCIATED METHODS

BACKGROUND OF THE INVENTION

This invention relates to telescopic spectacle assemblies and more particularly to a universally adjustable assembly for use with implanted intraocular lens assemblies.

As one can ascertain, the prior art is replete with many examples of intraocular lens assemblies. These lens assemblies are implanted in the eye of a patient and consist of an optic lens and haptic for fixation of the lens in a posterior or anterior chamber of the eye. Such implants have been devised in many different configurations and are useful for assisting visually handicapped persons.

For examples of such intraocular implants, reference is made to U.S. Pat. No. 4,681,585 entitled INTRAOCULAR IMPLANT issued on July 21, 1987 to R. Sayano et al. For further examples of such lenses reference is made to U.S. Pat. No. 4,681,586 issued on July 21, 1987 and entitled INTRAOCULAR LENS HAVING UNITARY INTEGRAL HAPTIC MEANS to R. L. Woods.

In any event, the intraocular lens has been extensively employed in regard to those patients which suffer from macular degeneration. Age related macular degeneration is the leading cause of visual loss in the United States of adults who are sixty years of age and older. Presently, it is estimated that over 150,000 people develop this disease each year. In regard to this particular disease there are two distinct types of macular degeneration which occur. A first type is known as atropic or 37 dry" type which results in a gradual atrophy of the sensory retina and pigment epithelium. A second type is referred to as the exudative or "wet" form. In this type new vessels proliferate from the choriocapillaris under the sensory retina which produce hemorrhaging and scarring This type of macular degeneration may be treated by laser photocoagulation providing that the neovascular tissue is outside the foveal avascular zone.

In any event, patients who have lost vision due to macular degeneration can be helped by optical aids such as high-plus lenses and telescopic assemblies that magnify an object to be viewed. The disadvantages are that high-plus lenses need to be held very close to the material or object and telescopic assemblies produce a very small visual field.

Hence the prior art attempted to improve the visual field of a telescope by using an intraocular lens as a high minus ocular. This procedure serves to enlarge the visual field three times greater than the external telescope. Unfortunately, using this system without spectacles makes the patient extremely myoptic and both central and peripheral vision can be lost. Hence there are new ocular lenses which have been developed which improve on such optical devices. In general such ocular lenses have a central portion which is either at a plus or a minus magnification and comprises a central zone in order to improve the patient's visual perception. In any event, all such devices are associated with spectacles which essentially form part of the telescopic assembly with the intraocular lens serving as the ocular lens component of the telescope and the spectacles or glasses serving as the objective lens. Hence in spite of the advances made in this particular field, there is still a need for an improved spectacle assembly to be worn by a person who has intraocular lenses implanted.

The design of such spectacle assemblies is difficult and, if not properly implemented, result in undesirable visual characteristics thus rendering it extremely difficult for the patient to see under various different circumstances. For examples of the problem and further examples of additional references as well as examples of improved intraocular lenses reference is made to a paper entitled 37 Optical Evaluation of Two New Intraocular Lenses for Age-Related Macular Degeneration" by J. Koziol et al. published by the Department of Opthalomogy, Eye and Ear Infirmary, University of Illinois, College of Medicine at Chicago. Reprint requests of this article can be obtained by writing to 1855 Taylor Street, Chicago, Ill. 60612 to Dr. Gholam A. Peyman. In any event, and as indicated, in spite of the above the most modern treatment requires the patient to wear a pair of spectacles which should be designed to accommodate the patient's particular visual problems. It is the design of the spectacles which enables the patient to obtain improved vision.

Hence as one can ascertain, such spectacles have to be designed with a consideration of many visual aspects required by a patient. The spectacles as designed must accommodate particular patient characteristics in order to enable proper vision in conjunction with an implanted intraocular lens assembly. Present systems do not deal with astigmatic (cylindrical) prescriptions and the use of present techniques do not accommodate for such astigmatism. Essentially, as one can ascertain, the persons who receive intraocular implants are defined as low-vision patients and their problems are unique.

The history has shown that dealing with the low-vision patient is much more complicated than one suspects in the beginning. In any event, alignment is critical to the patient's viewing success. One must take into consideration various aspects of the spectacle assembly which will enable a low-vision patient having an intraocular implant to view in a proper manner. Hence one must consider the pantascopic or retroscopic tilt which relates to the objective lens optical axis. A patient must be taught how to align the entire system as compared to mounting it on a pair of glasses. Other considerations such as binocularity are also extremely important.

In any event, one must also understand that after a lens is implanted and the patient's vision worsens then the telescopes that they employ will reach a condition where the patient will need more magnification than can be supplied with a single objective lens assembly. In this manner one cannot easily replace the spectacle assembly without major modifications. In any event, as one can ascertain from the above, the provision of a spectacle assembly for use with an implanted intraocular lens is an extremely important part of a total vision system.

It is therefore an objective of the present invention to provide an improved telescopic spectacle assembly for use with implanted intraocular lens assemblies.

It is a further objective of the present invention to provide a universally adjustable telescopic spectacle assembly for use with implanted intraocular lenses.

BRIEF DESCRIPTION OF THE PREFERRED EMBODIMENT

A method of providing increased visual acuity to the eye of a user having implanted in said eye an intraocular lens, which lens forms the ocular part of a telescope comprising the steps of positioning a universal moveable telescopic objective lens assembly in front of the eye of said user and moving said telescopic assembly until the user perceives with optimum visual acuity.

DETAILED DESCRIPTION OF THE FIGURES

Figure 1:
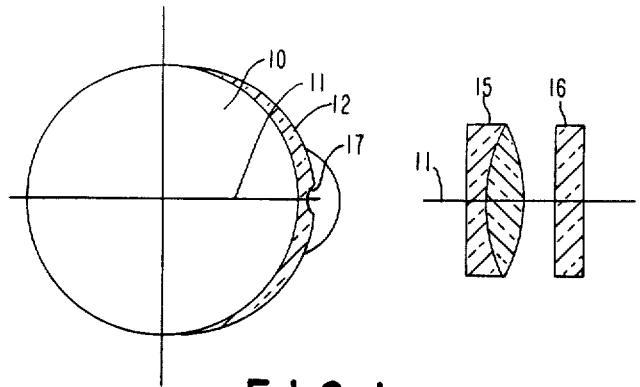
FIG. 1 is a side view depicting in diagrammatic form an intraocular lens operating in conjunction with a telescopic and cylindrical lens according to this invention.

Referring to FIG. 1, there is shown a simple schematic useful in explaining the nature of the present invention.

As one can ascertain from FIG. 1, there is shown a schematic portrayal of a human eye 10 which eye has implanted therein an intraocular lens assembly 12. The optical axis of the eye is designated by reference number 11. As further indicated, the intraocular lens has a central portion 17 which may be configured to be of a plus or a minus magnification as compared to the surrounding concentric lens portion. Such lenses 12 are available in many prior art designs. In any event, as indicated above, when an intraocular lens 12 is implanted in the eye of a patient, the patient still requires an optical assembly to be carried by a spectacle frame. Essentially, the optical assembly includes an objective lens 15 which forms the objective part of a telescopic arrangement. Also located in front of the objective lens assembly 15 is a cylindrical lens 16 The cylindrical lens 16 is positioned in front of the objective lens and provides for astigmatism correction or cylindrical correction and may for example be a +2 or +3 diopter lens assembly. The cylindrical lens 16 is of lower power than the objective lens assembly and is accommodated according to a given cylindrical prescription correction which is normally prescribed by the physician or practitioner.

Figure 2:
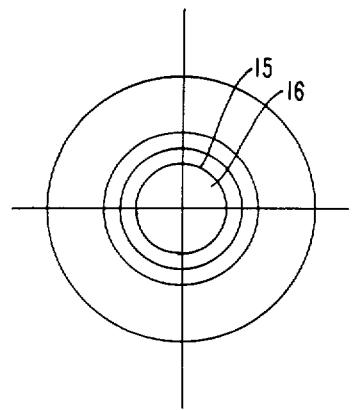
FIG. 2 is a front plan view of FIG. 1

Referring to FIG. 2, there is shown a front view of the assembly of FIG. 1 indicating that the cylindrical lens 16 is positioned in front of the objective lens assembly 15. As one can ascertain from FIG. 1, the entire telescopic arrangement which is necessary for proper vision of the subject includes the intraocular lens as lens 12 which forms the ocular of a typical telescopic assembly. The objective lens 15 forms the objective for the telescope while the cylindrical lens 16 is positioned in a fixed relationship from the objective lens and provides for cylindrical correction for the user. This then alleviates any astigmatism problems that the particular user may have.

Referring again to FIG. 1, as one will ascertain, the objective lens 15 may be a single lens objective or a air spaced or cemented doublet lens configuration. A typical objective lens may have a +23.5 diopter power available to work with typical intraocular lenses as lens 12 to provide a patient with telescopic viewing capability.

Figure 3:
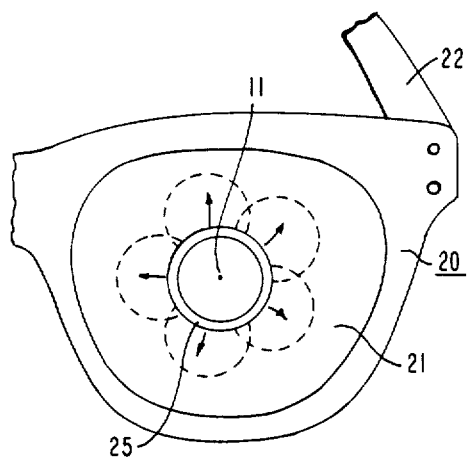
FIG. 3 is a front view in partial form of a spectacle arrangement employing a telescopic housing assembly which can shift around a central axis point.

Referring to FIG. 3, there is shown a front view of a spectacle assembly 20 which is utilized to hold the objective lens 15 and the cylindrical lens 16 of FIG. 1 before the eye 10 of a user. The user has implanted in his eye an intraocular lens 12. As one can ascertain from FIG 3, the spectacle assembly 20 is shown only as the left half. It is immediately noted that the right half of the frame has identical structure and has a carrier or test lens 21 which serves to support a telescopic arrangement 25. Essentially, the arrangement 25 is typical of many such telescope assemblies which are presently employed for improving the vision of low vision patients See for example the catalog of Designs for Vision, Inc. of Ronkonkoma, N.Y. which provides examples of expanded field spiral focus telescopes which telescopes are adapted to be carried by means of an ordinary lens support as 21 in conjunction with a frame 20.

As seen from FIG. 3, the structure allows the axis of the tubular assembly 25 to provide shifting of the objective lens axis about a central axis point as indicated by the dashed circles This can be accommodated by means of a suitable slot in the carrier lens assembly 21 whereby the user or practitioner can move the entire assembly 25 in all directions depicted by the arrows and the dashed lines of FIG. 3. Hence as one can immediately ascertain from viewing FIG. 3, one has the ability to concentrically shift the objective lens axis which lens is carried by the tubular member 25 around and about a central axis point as for example point 11 of FIG. 3 which essentially is indicative of the optical axis 11 as for example shown in FIG. 1.

Figure 4:
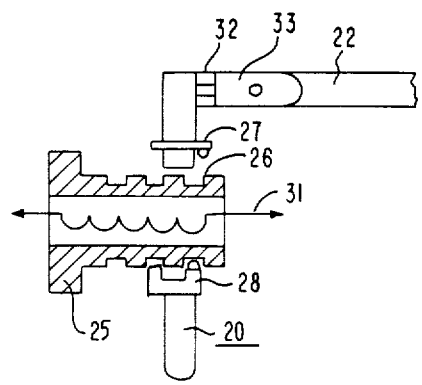
FIG. 4 is a side view showing a spiral motion of the telescopic assembly along the optical axis of the objective lens.

Shown in FIG. 4 is a side view of the tubular member 25. The tubular member 25 holds the cylindrical lens 16 and objective lens 15. The tubular member or assembly 25 is associated with a suitable spiral thread 26 which is formed about the peripheral surface of the tubular member. The spiral thread 26 is adapted to engage with two or more predetermined stop members as 27 and 28 each of which member has a projecting tip which can engage the spiral thread mechanism 26 to enable a practitioner to rotate or move the entire assembly 25 in the directions indicated by arrow 31 and thereby move it in and out which movement is associated with a spiral motion along or parallel to the optical axis 11 of the objective lens.

Thus as one can immediately ascertain from FIGS. 3 and 4, the entire mechanism 25 is positioned with respect to the carrier lens 21 so that it can move in all relationships as shown in FIG. 3 as well as in those directions shown in FIG. 4.

Referring to FIG. 5, again the telescopic assembly 25 is depicted and is associated with a new series of arrows indicating that the assembly 25 as mounted in the carrier lens 21 and associated with the frame 20 includes an all-way pivotal joint mechanism to permit maximum oblique adjustment which adjustment is related to the optical or central axis 11. Thus as one can ascertain from reviewing FIGS. 3, 4, and 5, the spectacle assembly as accommodated by the housing 25 enables universal adjustment of the telescopic assembly in all directions. In this manner the following advantages are obtained and achieved by the techniques depicted.

As indicated above, alignment is critical to the patient's success in viewing objects. In order to properly align an objective assembly with an intraocular lens which becomes a telescopic system, one must consider the pantascopic or retroscopic tilt relating to the objective lens optical axis 11. This is accommodated by the modes of motion depicted in FIGS. 3 and 5. In this manner, a patient or a practitioner can be taught how to align this system as compared to fixedly mounting any such system on a pair of spectacles using conventional techniques such as spacer rings and so on.

Figure 5:
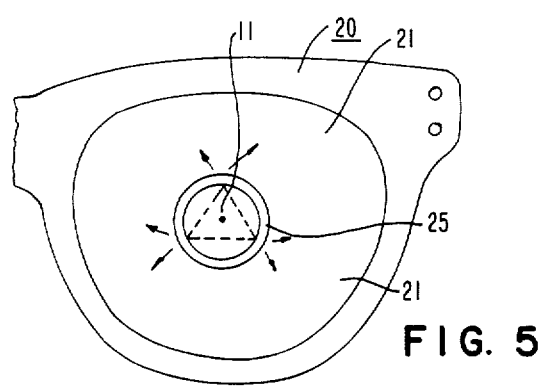
FIG. 5 is a front view similar to FIG. 3 showing the pivotal aspects of the particular apparatus according to this invention.

Based on the motions afforded again in FIGS. 3 and 5, one can completely compensate for all binocularity problems associated with the patient to enable the patient to achieve good vision at near distances as well as good vision at far distances. As one can ascertain, after an intraocular lens 12 is implanted and the patient's vision changes, it will reach a point where the intraocular lens would not be sufficient to supply the necessary magnification that is further afforded with the use of the objective lens 15. Based on the above techniques, the patient now has the ability to further adjust the telescopic assembly 25 so that the objective lens can be moved closer or further from the eye thereby compensating for the long term effects in regard to the vision of the patient. In this manner the patient can also achieve a higher magnification when such a magnification is desired.

Figure 6:
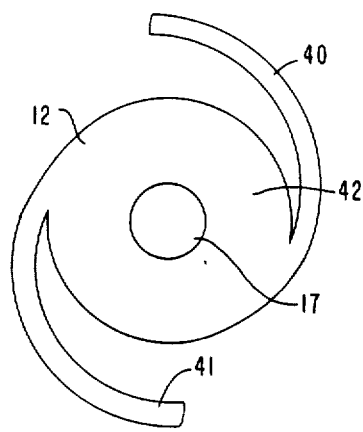
FIG. 6 is a front diagrammatic view depicting a typical intraocular lens of the type employed in conjunction with this invention.

Referring to FIG. 6, there is shown a typical intraocular lens assembly. Essentially, the lens assembly depicted in FIG. 6 has a peripheral concentric lens portion 42 with a concentric central area or portion 17. The area 17 may be a +or a −lens area which serves to improve the near vision capabilities of the patient. The typical intraocular lens as lens 12 is associated with haptics as 40 and 41 which are used to implant the lens within an appropriate chamber of the eye of the patient as indicated above.

Apart from such considerations and referring again to FIG. 4, there is shown a hinge assembly which consists of a typical hinge 32 coupling the temple piece 22 to the front of the frame assembly with a adjustment mechanism 33 to enable tilting of the front spectacle frame or carrier lens with respect to the eyes of a patient This provides another degree of motion which is available for the patient. Such techniques for supporting or carrying telescopic assemblies are known in the art and for example are described in the following patents.

See for example U.S. Pat. No. 4,364,645 issued on Dec. 21, 1982 entitled ADJUSTABLE FRAME APPARATUS FOR TELESCOPIC SPECTACLES issued to William Feinbloom and assigned to the assignee herein. As one can ascertain from that patent, the mechanism depicted will enable the motion shown for example in FIG. 3 and the telescopic assemblies which are analogous to assembly 25 can also be moved as desired within apertures located in the carrier lens assemblies 21. The patent also shows a hinge assembly as in FIG. 4 of the patent which will enable the tilting of the entire spectacle frame with respect to the temple piece 22. As indicated above, the assembly as depicted in that patent shows means for obtaining inclination at the temples utilizing such techniques as exemplified by the teachings of U.S. Pat. No. 4,364,645.

See also U.S. Pat. No. 4,498,743 issued on Feb. 12, 1985 to William Feinbloom and assigned to the assignee herein and entitled BINOCULAR FIELD OF VIEW SIMULATOR. That patent also discloses various adjustable mechanisms associated with a trial frame or spectacle frame to provide various different types of motion to a lens assembly associated with said frame.

Figure 7:
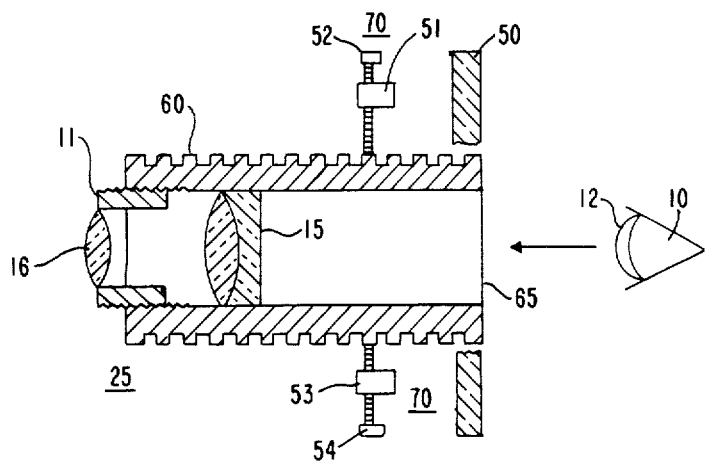
FIG. 7 is a side view in partial cross section depicting a telescopic assembly which can be employed in combination with a spectacle lens.
Figure 8:
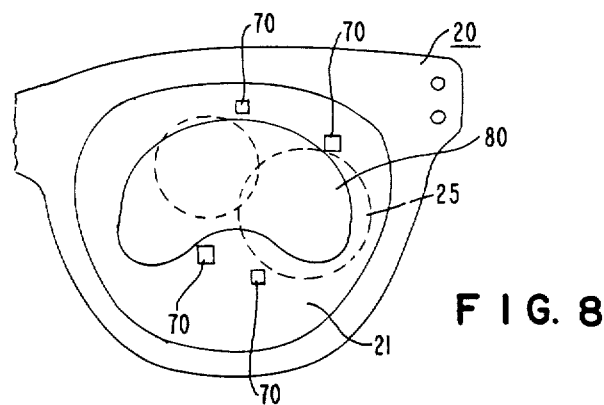
FIG. 8 depicts a partial view of a spectacle lens having a shaped aperture to accommodate the telescopic assembly according to this invention.

Referring to FIG. 7, there is shown a cross sectional view of a tubular assembly 25 which can be employed to implement the various modes of motion as indicated for examples in FIGS. 3, 4, and 5. Essentially, as one can ascertain from FIG. 7, the eye of the observer is shown and referenced by reference numeral 10 and has implanted therein an intraocular lens 12. The tubular assembly 25 has on the outer periphery a spiral thread configuration 60. Inside the tube assembly at an appropriate distance from the viewing end 65 is mounted the objective lens assembly as 15 of FIG. 1. Also separately mounted in an additional tubular assembly 61 is the cylindrical lens 16. As one can see, the entire tubular assembly 25 can move forwards or backwards in a spiral path by means of two members designated by reference numeral 70. Each member 70 has an extending post 51 which is rigidly secured to the carrier lens 21 or frame as shown in FIG. 8 and each is associated with a movable screw member as member 52 associated with post 51 and member 54 associated with post 53. In this manner, the screws associated with each member as screws 52 and 53 are directed onto the threaded spiral configuration 60 of the housing section 25. Accordingly, the entire objective lens assembly can move in and out as depicted in FIG. 3.

At the same time, the telescopic assembly 25 is placed within an arcuate shaped aperture as aperture 80 associated with the carrier lens 21. As shown by the dashed circles, the entire assembly can be moved in the directions as for example shown in FIGS. 3 and 5. When a proper orientation of the telescopic assembly 25 is made by either the user or the practitioner, the screw members 52 and 53 are then more tightly engaged into the corresponding surface threads associated with the housing 25. The cylindrical lens 16 by means of the separate housing 61 can also be moved in order to compensate for the cylindrical prescription of the handicapped user with respect to the objective lens 15.

It is, of course, immediately apparent that while FIGS. 6 and 7 show an operational type of unit capable of affording the adjustment modes depicted in FIGS. 3–5, it is of course understood that various other techniques and mechanisms can be employed as it should be obvious to those skilled in the art on how to accommodate and accomplish the universal motion modes required and necessary in order to enable a person having an implanted intraocular lens to obtain maximum visual acuity. It is also noted tat the shape of the aperture 80 can vary depending upon the exact requirements of the particular user.

By using such shaped apertures as 80 and as evidenced by reference to the above-noted patents, one can also vary the interpupilary distance as well as employing a flexible hinge to vary the tilt of the front of the spectacle assembly with respect to the temple pieces. It thus should be apparent that the universal motion afforded by the above-described invention will enable a person having an implanted intraocular lens to fully compensate for all visual defects as described above and to enable him to use the spectacle assembly for long periods of time during which his vision requirements may change.

It is understood that vision is subjective and hence the above described invention allows a user to make the subjective determination as to his visual perception. This is of extreme importance to low vision patients and patients in general as each individual requires and demands particular forms of visual acuity in order for such individuals to lead a productive life.

I claim:

1. A method of providing increased visual acuity to the eye of a user having implanted in said eye an intraocular lens, which lens forms the ocular part of a telescope comprising the steps of:
positioning a universal moveable telescopic objective lens assembly in front of the eye of said user and moving said telescopic assembly until the user perceives with optimum visual acuity.

2. The method according to claim 1, wherein said universal moveable telescopic lens assembly is moveable in a first mode such that the axis of said objective lens is moved about a central axis point aligned with the optical axis of said lens.

3. The method according to claim 2, wherein said universal moveable lens assembly is moveable in a spiral motion path parallel to said optical axis.

4. The method according to claim 1, wherein said universal moveable telescopic lens assembly is moveable in a third mode in directions oblique to said optical axis.

5. The method according to claim 1, further including the step of positioning a cylindrical lens in front of said objective lens.

6. The method according to claim 5, further including the step of moving said cylindrical lens in accordance with the movement of said objective lens in directions parallel to said optical axis.

7. The method according to claim 1, wherein the step of positioning said universally moveable telescopic objective lens assembly includes the steps of placing said assembly in a spectacle frame which frame is supported on the face of said user in front of said user's eye and positioning said assembly with respect to said supported frame.

8. The method according to claim 7, wherein the step of placing includes placing said objective lens assembly in an arcuate aperture located on said spectacle frame and in the vicinity of the eye of said user.

9. The method according to claim 1, wherein said intraocular lens is of the type having an central lens portion of a different magnification characteristic from the surrounding concentric lens portion.

10. The method according to claim 1, wherein said intraocular lens is implanted in the posterior chamber of said user's eye.

11. The method according to claim 1, wherein said intraocular lens is implanted in the anterior chamber of said user's eye.

12. Apparatus for providing a telescopic magnifying assembly for a patient's eye adapted to receive therein an intraocular lens which lens forms the ocular portion of said telescopic magnifying assembly comprising:
a spectacle frame having at least one test carrier lens emplaced in the eyepiece of said frame, said lens including an elongated aperture,
a telescopic objective lens assembly having a given optical axis positioned in said aperture and moveable with respect to said aperture in a first mode to spirally move said lens parallel to said optical axis, and moveable in a second mode to shift said objective lens about said optical axis and moveable in a third mode to move said lens oblique to said optical axis, to thereby provide optimum visual acuity for said patient when said frame is accommodated on the face of said patient.

13. The apparatus according to claim 12, further including inclination means coupling at least one temple piece of said frame to the front of said frame carrying said lens to enable tilting of said front with respect to said temple.

14. The apparatus according to claim 12, further including a cylindrical lens positioned in front of said objective lens for providing astigmatism correction to the eye of said user.

15. The apparatus according to claim 14, wherein said cylindrical lens is of a lower optical power than said objective lens.

16. The apparatus according to claim 14, further including means coupled to said cylindrical lens for moving the same with respect to said objective lens.

17. The apparatus according to claim 12, wherein said intraocular lens is of the type having a central lens portion of a different optical power than a concentric surrounding lens portion.

18. The apparatus according to claim 12, wherein said objective lens assembly is a single lens.

19. The apparatus according to claim 12, wherein said objective lens assembly is a doublet lens assembly.

20. The apparatus according to claim 12, further including means mounted on said frame and positioned to coact with said telescopic lens assembly to lock said assembly in a given position on said frame after adjustment of said assembly according to said movement provided by said first, second and third modes.

* * * * *